US00PP13720P29

(12) United States Plant Patent
Roberts

(10) Patent No.: US PP13,720 P2
(45) Date of Patent: Apr. 8, 2003

(54) MINT PLANT NAMED 'AQUAMINT'

(75) Inventor: Donald D. Roberts, Corvallis, OR (US)

(73) Assignee: Premier Botanicals Limited, Independence, OR (US)

( * ) Notice: Subject to any disclaimer, the term of this patent is extended or adjusted under 35 U.S.C. 154(b) by 0 days.

(21) Appl. No.: 10/012,267

(22) Filed: Nov. 6, 2001

(51) Int. Cl.[7] ..... A01H 5/00
(52) U.S. Cl. ..... Plt./259
(58) Field of Search ..... Plt./259, 258

(56) References Cited

PUBLICATIONS

Aviv, D. And E. Galun, "Biotransformation of Monoterpenes by Mentha Cell Lines: Conversion of Pulegone to Isomenthone," *Planta Medica* 33:70–77 (1978).

Hefendehl, F. W. and Merritt J. Murray, "Changes in Monoterpene Composition in *Mentha aquatica* Produced by Gene Substitution," *Phytochemistry 11*:189–195 (1972).

Nigam, Ishwar C. and Leo Levi, "Essential Oils and Their Constituents XX, Detection and Estimation of Menthofuran in *Mentha arvensis* and Other Mint Species by Coupled Gas–Liquid—Thin–Layer Chromatography," *Journal of Pharmaceutical Sciences 53*:1008–1013 (1964).

Roberts, D. D. and C. E. Horner, "Sources of Resistance to *Puccinia menthae* in mint," *Plant Disease 65*:322–324 (1981).

Stace, Clive, "New Flora of the British Isles," Cambridge University Press, Family Lamiaceae, Genera Mentha, pp. 680–686 (1991).

*Primary Examiner*—Bruce R. Campell
*Assistant Examiner*—June Hwu
(74) *Attorney, Agent, or Firm*—Klarquist Sparkman, LLP

(57) ABSTRACT

A new and distinctive variety of a water mint plant of the species botanically known as *Mentha×aquatica* L, named 'Aquamint' which has an upright growth habit, produces a unique mint oil and is resistant to mint rust caused by *Puccinia menthae* and mint wilt caused by *Verticillium dahliae*.

3 Drawing Sheets

LATIN NAME OF THE GENUS AND SPECIES OF THE PLANT CLAIMED

*Mentha×aquatica* L. 'Aquamint'.

VARIETY DENOMINATION

'Aquamint'.

Selection 81-019-16 is a new *Mentha×aquatica* L. plant that has resistance to mint wilt (*Verticillium dahliae*) and mint rust (*Puccinia×menthae*) and has a more upright growth habit than its seed parent. I have named my new cultivar 'Aquamint.' The growth and biomass production of 81-019-16 under field conditions resembles that of 'Black Mitcham' peppermint (*Mentha×piperita* L.). The oil produced by this plant has the same components as commercial peppermint but in different concentration ratios. The major components of the oil from 81-019-16 are menthofuran, and pulegone.

This new mint was discovered in a mint breeding program in which the primary objective was to develop a mint with a high concentration of menthofuran and other chemical components common in peppermint oil. The oil from this plant was designed to be blended with mint oils low in menthofuran and other components to improve their quality. The secondary objective of the program was to introduce resistance to the mint diseases, Rust caused by *Puccinia menthae* and Wilt caused by *Verticillium dahliae*. The new plant was discovered in a cultivated area on land near Corvallis, Oreg., and was initially identified as 81-019-16.

Selection 81-019-16 originated as a seedling from a polycross where the female (seed) parent was a *Mentha aquatica* L. plant identified as M-0100 (proprietary, unpatented) in our germplasm collection. Parent M-0100 is male sterile and rarely, but occasionally, outcrosses with other Mentha species. The pollen parent is unknown, but the pollinator in the polycross came from other Mentha species (proprietary, unpatented) plants in our collection. Seedlings that developed from seeds collected from the female parent were planted in observation plots where plant vigor and disease development were recorded. Selected seedlings were harvested for oil collection. Selection 81-019-16 was found to have the characteristics of vigorous growth, disease resistance and an oil composition that satisfied the objectives of the breeding program.

Asexual reproduction of 81-019-16 was conducted each year under my direction since 1981 at a research farm and greenhouses near Corvallis, Oreg. Asexual reproduction has been conducted by rooting stem cuttings and by planting stolon taken from field grown plants. Characteristics of 81-019-16 in so far as they have been observed are firmly fixed, come true-to-form and are established and transmitted in succeeding generations through vegetative propagation.

BRIEF DESCRIPTION OF THE PHOTOGRAPHS

The accompanying color photographs show typical, field grown specimens of the vegetative growth of my new mint plant and depict the color as nearly true as is reasonably possible to make the same in a color illustration of this character. It should be noted that colors vary with growing conditions and time of year as well as with lighting conditions at the time the photographs are taken.

DETAILED DESCRIPTION

The new mint plant produces a unique mint oil and is distinct from other mint plants in several characteristics, including but not limited to the following:

1. Has a more vigorous, upright growth than its parent.
2. Produces many runners (stolon) and rhizomes that cause the rapid spread (expansion) of the plant.
3. Produces an oil with similar chemical components, but with different concentrations, as peppermint (*M. piperita*× L.).
4. Produces an oil with a composition of from about 35 to 55 percent menthofuran when the whole plant is processed.
5. Produces an oil suitable for blending with peppermint oils low in menthofuran.
6. Has a higher level of resistance to mint wilt (*V. dahliae*) than 'Black Mitcham' peppermint.
7. Is resistant to mint rust caused by *Puccinia menthae*.

Figure 1:
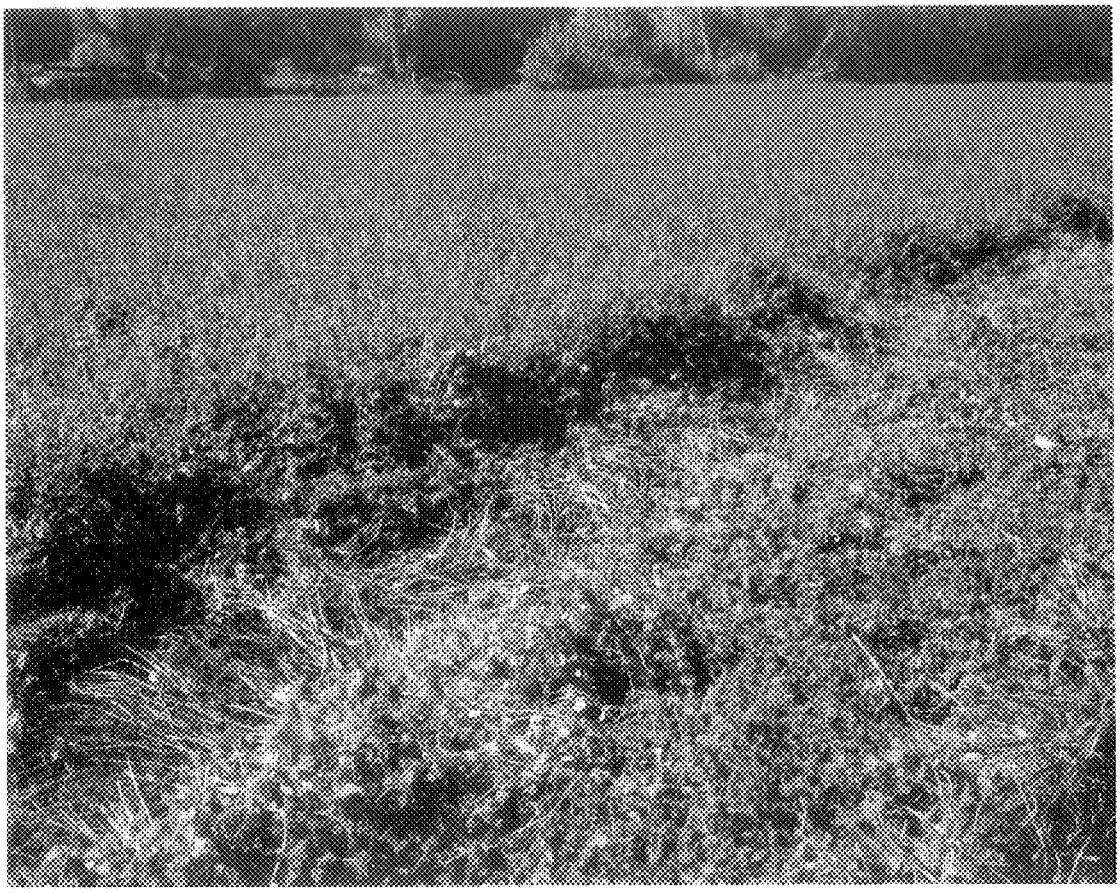
FIG. 1 illustrates the vigorous growth and biomass production under field conditions of my new mint plant in accordance with the present invention.

The vigor of 81-019-16 ('Aquamint') is illustrated in FIG. 1 where a swath of the mint was cut in our research plot. In this two-year old field, the mint grew to over two feet in height, formed a solid canopy with row spacing of 2 feet and the density of plant material was equal or greater than that of a typical commercial field of *M.×piperita* variety 'Black Mitcham' peppermint. The upright growth habit of 81-019-16 is also illustrated in FIG. 1. This is a selected trait that makes it different from its seed parent, and is important for commercial harvest considerations. FIG. 1 also illustrates the uniform growth, establishment, and maturity of plants in this field that is two years old.

Figure 2:
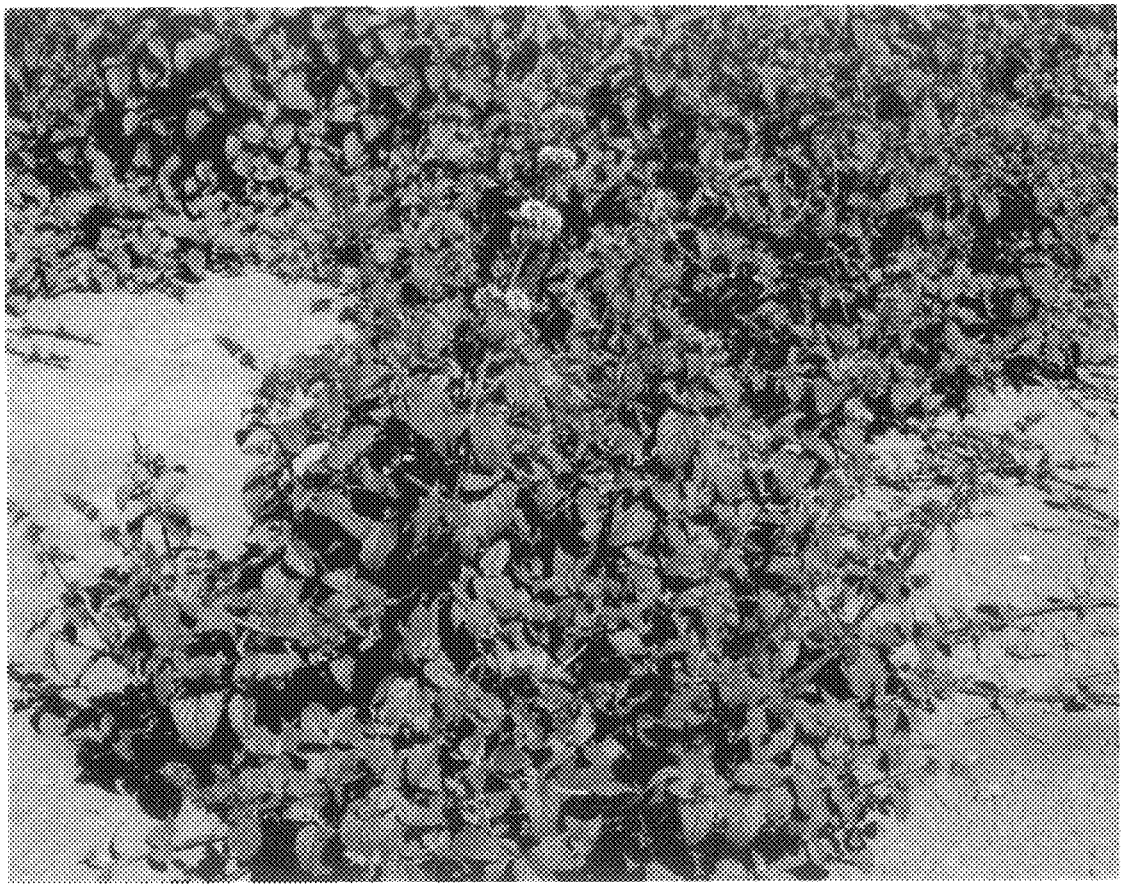
FIG. 2 illustrates the vigorous production of stolon under field conditions of my new mint plant in accordance with the present invention.

FIG. 2 illustrates the development of runners on a field grown plant. Commercially, mint is vegetatively propagated by harvesting the runners and underground rhizomes that are then planted to establish new fields. The spread of the new plants is dependent on the growth of runners and underground rhizomes and is necessary to establish a solid stand as illustrated in FIG. 1.

Figure 3:
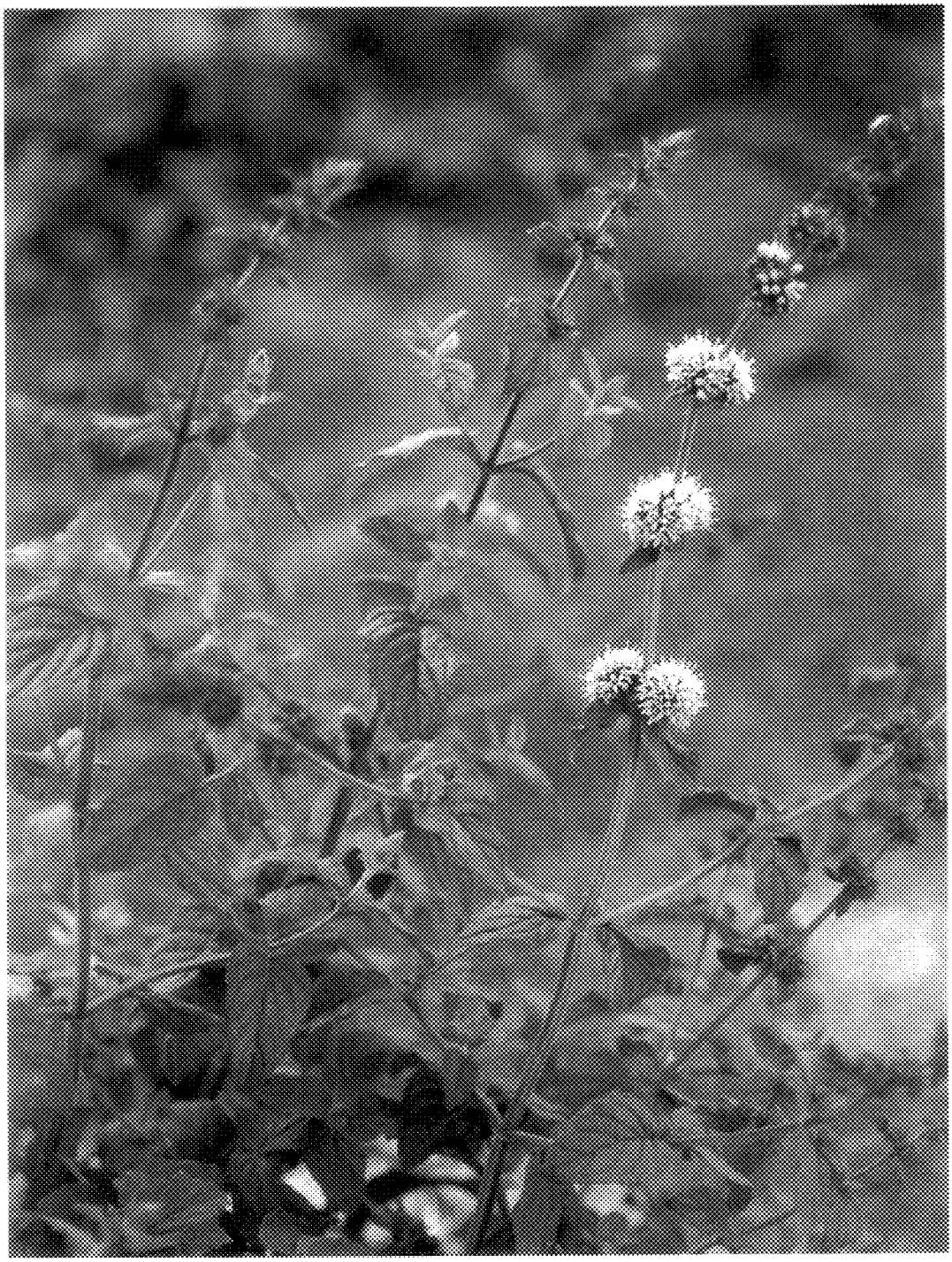
FIG. 3 illustrates the inflorescence and flowering pattern of my new mint plant in accordance with the present invention.

FIG. 3 illustrates the flowering pattern and shape of the floral head. The large flower head is important in oil yield and quality. The mature flower produces most of the oil that contributes to its high menthofuran content as shown in Table 1. Oil distilled from the flowers of my new variety in our test contained about 65.8 percent menthofuran and about 10.6 percent pulegone compared with oil from the whole plant (including the flowers) of my new variety with about 40.1 and about 8.1 percent, respectively.

TABLE I

Composition of 81-019-16 mint oil distilled from whole plant and flowers in our test.

| Components* | Whole Plant | Flowers |
|---|---|---|
| α-Pinene | 1.2 | 0.8 |
| β-Pinene | 1.8 | 1.1 |
| L-Limonene | 5.3 | 4.9 |
| 1,8-Cineole | 8.4 | 8.4 |
| 3-Octanol | 0.4 | 0.0 |

TABLE I-continued

Composition of 81-019-16 mint oil distilled from whole plant and flowers in our test.

| Components* | Whole Plant | Flowers |
|---|---|---|
| L-Menthone | 4.1 | 1.4 |
| Menthofuran | 40.1 | 65.8 |
| D-Isomenthone | 1.0 | 0.0 |
| Menthyl acetate | 8.0 | 1.4 |
| Neo-menthol | 0.5 | 0.0 |
| β-Caryophyllene | 0.8 | 0.4 |
| L-Menthol | 5.4 | 1.8 |
| Pulegone | 8.1 | 10.6 |

*Expressed as percent composition and based upon the analysis of the respective mint oils by gas chromatography. Percentages are determined by calculation of the relative peak areas.

It should be noted that the chemical composition of plants can vary with growing and lighting conditions, but conventional processing of whole plants of my new variety yields oil that is about 35% to 55% menthofuran.

The menthone and menthol that are in the whole plant oil come mostly from the foliage and not the flower. The association of pulegone and menthofuran in the flower of 81-019-16 is expected because pulegone is the precursor to menthofuran in the biosynthetic pathway of the components of mint oil. Both compounds are minor components in commercial peppermint (*M.×piperita*) oil.

Selection 81-019-16 is more vigorous and has a more upright growth habit than its seed parent M-0100. Over a two-year period, my new mint variety grew to over two feet in height and the density of plant material was equal to or greater than that of a typical commercial field of 'Black Mitcham' peppermint. However, the oil from both plants has a similar composition (Table II). Both the parent and progeny have menthofuran as the major component in their oils and it occurs in the low 40 to mid 50 percent range. Pulegone occurs at near 8 percent in both oils.

The oil from seedling 81-019-16 and the seed parent M-0100 are similar and both are different from certain tested commercial peppermint oils (Table II). The data shows the difference between the concentrations of menthofuran and pulegone in selection 81-019-16 and that in the commercial mint oils from *M. arvensis* and *M.×piperita*. The commercial *M. arvensis* oil has been partially dementholized. Menthone occurs at 4.1 percent in selection 81-019-16 and at 21.7 and 17.6 percent in *M. arvensis* and *M.×piperita*, respectively. Menthofuran occurs at 40.1 percent in selection 81-019-16 and in the commercial oils at less than 3 percent. Pulegone occurs at 8.1 percent in selection 81-019-16 and less than 1 percent in the commercial oils.

The ability to increase the concentration of menthofuran and pulegone in commercial mint oils is possible by blending such commercial mint oil with oil from selection 81-019-16. The other components in the commercial mint oils would not be significantly changed in such a blend because of the relatively low concentrations of the other components present in selection 81-019-16. In this respect, selection 81-019-16 meets the objective of the breeding program in that it produces an essential oil that can be blended with commercial mint oils to impart a higher menthofuran content.

TABLE II

Major components of oil from selection 81-019-16, female parent M-0100, and commercial peppermint oils from India and the United States in our test.

| Components* | 81-019-16 | Seed parent M-0100 | India Peppermint *M. arvensis* | U.S. Peppermint *M.x piperita* |
|---|---|---|---|---|
| α-Pinene | 1.2 | 0.7 | 1.6 | 0.8 |
| β-Pinene | 1.8 | 0.9 | 1.9 | 1.0 |
| L-Limonene | 5.3 | 4.0 | 3.4 | 1.5 |
| 1,8-Cineole | 8.4 | 4.5 | 0.7 | 4.8 |
| 3-Octanol | 0.4 | 0.0 | 1.2 | 0.3 |
| L-Menthone | 4.1 | 1.3 | 22.6 | 17.6 |
| Menthofuran | 40.1 | 43.7 | 0.0 | 3.0 |
| D-Isomenthone | 1.0 | 3.1 | 12.1 | 2.7 |
| Menthyl acetate | 8.0 | 10.1 | 2.4 | 6.7 |
| Neo-menthol | 0.5 | 2.7 | 5.1 | 5.4 |
| β-Caryophyllene | 0.8 | 2.5 | 1.3 | 1.2 |
| L-Menthol | 5.4 | 5.5 | 39.8 | 47.3 |
| Pulegone | 8.1 | 8.9 | 0.9 | 0.7 |

*Expressed as percent composition and based upon the analysis of the respective mint oils by gas chromatography. Percentages are determined by calculation of the relative peak areas.

Listed in Table III are the analyses of oil from selection 81-019-16 collected in five different years. The data presented for 1982 and 1995 are analyses of oil distilled from plants grown in small research plots and processed on a small, pilot size distillery. The data presented for 1998, 1999, and 2000 are analyses of oil distilled from plant grown in a commercial size plot and processed in a commercial mint distillery. The menthofuran content of the oils in 1982 and 1995 are higher because cultural practices in the research plots and the distillation process were more closely monitored than was possible on the commercial size operation in 1998, 1999, and 2000.

The concentration of components in the oil of this new mint variety can be significantly affected by plant maturity. This is illustrated in Table III with the concentration of menthofuran in different years. Management factors played a role in the menthofuran content between the first two years and the last three years, but maturity of the plant at harvest contributed to the difference in concentration in years 1998, 1999, and 2000. If harvested too early and the flower heads are not developed, the menthofuran concentration will be lower and the pulegone will be higher. We have observed that the temperature in which a commercial mint still distills mint can affect the amount of menthofuran in the resulting mint oil. Mint oils collected from our pilot size distillery were processed at a higher temperature than what is normally used in a commercial mint distillery. Hence, a more complete distillation is achieved and a higher concentration of menthofuran occurs in the oil as observed in years 1982 and 1995.

TABLE III

Major components of oil from processing whole plants (including flowers) of selection 81-019-16 produced over 8 years.

| Components* | 1982[a] | 1995[a] | 1998[b] | 1999[b] | 2000[b] |
|---|---|---|---|---|---|
| α-Pinene | 0.9 | 1.1 | 1.3 | 0.8 | 1.1 |
| β-Pinene | 1.7 | 1.9 | 1.9 | 1.8 | 1.7 |
| L-Limonene | 4.7 | 5.2 | 6.2 | 5.3 | 5.1 |
| 1,8-Cineole | 8.0 | 8.9 | 9.5 | 8.4 | 7.8 |
| 3-Octanol | 0.0 | 0.0 | 0.0 | 0.4 | 0.0 |
| L-Menthone | 1.5 | 1.6 | 5.0 | 4.1 | 4.0 |

TABLE III-continued

Major components of oil from processing whole plants (including flowers) of selection 81-019-16 produced over 8 years.

| Components* | 1982[a] | 1995[a] | 1998[b] | 1999[b] | 2000[b] |
|---|---|---|---|---|---|
| Menthofuran | 48.8 | 51.7 | 44.2 | 40.1 | 36.4 |
| D-Isomenthone | 0.4 | 0.4 | 1.0 | 1.0 | 0.9 |
| Menthyl acetate | 5.4 | 5.2 | 4.4 | 8.0 | 8.0 |
| Neo-menthol | 0.4 | 0.3 | 0.5 | 0.5 | 1.1 |
| β-Caryophyllene | 1.7 | 1.7 | 0.9 | 0.8 | 1.0 |
| L-Menthol | 1.7 | 1.7 | 5.2 | 5.4 | 11.5 |
| Pulegone | 7.1 | 7.1 | 10.0 | 8.1 | 8.5 |

*Expressed as percent composition and based upon the analysis of the respective mint oils by gas chromatography. Percentages are determined by calculation of the relative peak areas.
Tests involved:
[a]experimental pilot size distillation and
[b]commercial size distillation.

Taxonomic Description of 81-019-16

Color references are to The Royal Horticultural Society (R.H.S.) Colour Chart, Royal Horticultural Society, London, United Kingdom, unless the context clearly indicates the color term is intended to have its ordinary dictionary meaning. Again, color can vary with growing and lighting conditions. Plant size can also vary with growing and lighting conditions.

Selection 81-019-16 is an upright bush type plant with lateral branches typical at each node of the main stem. The height and spread of 81-019-16 will vary based on cultural management practices and other known factors that effect plant growth patterns. The height of 81-019-16 is generally equivalent to that of 'Black Mitcham' when grown under similar conditions in the Corvallis area of the Willamette Valley of Oregon, USA. In the first year after planting (baby year) the average height of field grown 'Aquamint' plants is 30 cm. Two year old plants grow from 0.75 to 1.0 m. Numerous upright stems grow from the stolons and secondary branching from the main stem occurs to form a compact growth habit. The average speed of runners produced by an 'Aquamint' plant in the first year is 1 to 1.25 m (under field conditions as of this time, observed in Corvallis, Oreg.) For a mature plant, i.e., a plant in full bloom, the main stem at mid-plant (approximately between the ninth and twelfth node) is typically 4–8 mm in width, while the secondary branch stems are typically 2–4 mm in width.

Lower leaves at the bottom of 81-019-16 ('Aquamint') plant stems are ovate lanceolate, while leaves on secondary branches and immature upper leaves are more lanceolate. The mature leaves range in color from R.H.S. Color Code 136B to 137B and immature upper leaves range in color from R.H.S. Color Code 137B to 138B. The mature lanceolate leaves are about two and one half time long as wide. Mid-main stem leaf size at flowering is typically about 20–30 mm in width and about 50–60 mm in length. Leaf size on secondary branches at flowering depends on the location on the branch. The leaves on secondary branches closest to the main stem are about one half the size of mature leaves on the main stem. The leaves are serrate, irregularly dentate and the apex is acute. Leaf base on 81-019-16 is rounded to slightly cordate. The top leaf surface is dark green in color, ranging from R.H.S. Color Code 136 B to 137 B. The lower leaf surface is lighter green ranging from R.H.S. Color Code 138 A to 138 C. Leaf venation is pinnate with the main vein being reddish-purple in color (ranging from R.H.S. Color Code 185B to 186B) from anthocyanin pigment development. Veins are prominent in all leaves. Veins on the ventral surface are pubescent while the interveinal area is puberulent. The upper leaf surface is puberulent. The texture of leaves range from moderately thick and rigid in mature leaves to velvety and soft in young leaves.

The main stem of 'Aquamint' is square, 5 to 7 mm thick at mid-stem, hard and woody at the base. The mature stem is pubescent, with the immature stem being more soft and velvety to the touch. Small lateral branches may be square to mostly round with flat sides and pubescent. Anthocyanin pigments are present in the immature terminal stem and tend to be less obvious as the stem matures. The mature stem does have flecks or streaks of anthocyanin present. The typical mature stem color ranges from R.H.S. Color Code 138C to 139C and immature stem color ranges from R.H.S. Color Code 185C to 186C.

Mature leaf petioles on the main stem are 5–8 mm in length while the petioles on secondary branch stem leaves are sessile to about 3 mm in length. The petioles range in color from R.H.S. Color Code 138 A to 138 C. Petioles of mature leaves becomes rigid compared to flexible petioles on young leaves.

The inflorescence of 81-019-16 forms verticils (cymes). The whorls, two per node, one in each leaf axil, are similar to *M. arvensis*, but with small bracts similar to *M. aquatica*. The cyme is composed of an average of 35 florets that ranges from about 30 to 40. The whorl of florets forms a rounded capitulum 15 to 20 mm wide.

The flower (floret) is small, 5 mm in length, irregular, bilabiate, and perfect. The gynoecium consists of a single pistil with a two-lobed stigma that is exserted. The androecium consists of four included stamen if present. Stamen may not always be present. The corolla is 5 lobed with two fused lobes to appear almost as one, and light lilac in color, ranging from R.H.S. Color Code 76C to 76D.

The calyx is campanulate with five acuminate teeth, slightly pubescent in texture, and generally green in color (R.H.S. Color Code 138 A), but with some anthocyanin present (R.H.S. Color Code 59 B to 60 B), often only on one side of the calyx. The calyx ranges from 2.5 to 3 mm in length, and 1.5 mm diameter at the top, and is slightly pubescent in texture.

The pedicel is consistently about 3 mm in length with reddish-purple color (R.H.S. Color Code 59 B to 60 B), and slightly pubescent in texture.

The peduncle is light green in color (R.H.S. Color Code 138 A to 138 C) and ranges in length from sessile on immature inflorescences to 20 mm on mature inflorescences.

The foliage and inflorescence have a minty fragrance with a slight aroma of chocolate and coconut.

Seed are rarely produced by 81-019-16, but when present the seed are 0.4 to 1.0 mm in diameter and typically range from R.H.S. Color Code 200A to 200D or R.H.S. Color Code 2002A.

The taxonomy of my new mint strongly suggests that it is a hybrid plant from *M. aquatica*, but with a male parent of unknown species. Oil characteristics from 81-019-16 are similar to *M. aquatica*, the inflorescence is similar to *M. arvensis*, and the growth habit is similar to *M.×smithiana*. Flow Cytometry data indicates the DNA content of 'Aquamint' is the same as that of a 96 chromosome *M. aquatica*.

I claim:

1. A new and distinct variety of *Mentha×aquatica* L. plant named 'Aquamint' substantially as shown and described herein.

* * * * *